United States Patent [19]

David et al.

[11] Patent Number: 4,650,757

[45] Date of Patent: Mar. 17, 1987

[54] PROCESS OF ENZYMATIC CONVERSION OF POLYSACCHARIDES

[75] Inventors: Marie-Henriette David, Ghent; Horst Günther, Overijse; Jean-Claude de Troostembergh, Tielt-Winge, all of Belgium

[73] Assignee: CPC International Inc., Englewood Cliffs, N.J.

[21] Appl. No.: 737,310

[22] Filed: May 23, 1985

[30] Foreign Application Priority Data

Jun. 5, 1984 [GB] United Kingdom ............... 8414272

[51] Int. Cl.$^4$ .................. C12P 19/20; C12P 19/14; C13J 1/00; C12R 1/11
[52] U.S. Cl. ............................. 435/96; 435/99; 435/276; 435/837; 426/52
[58] Field of Search ............... 435/96, 99, 98, 276, 435/837; 426/12

[56] References Cited

U.S. PATENT DOCUMENTS 3,888,738 6/1975 Okada et al. .................. 435/193
4,284,722 8/1981 Tamuri et al. ................. 435/96 X
4,469,791 9/1984 Colson et al. ................. 435/253

OTHER PUBLICATIONS

Kitahata, et al, Agr. Biol. Chem., 38, 387–393, 2413–2417 (1974).
Kitahata, et al, Agr. Biol. Chem., 39, 2185–2191 (1975).
Stark, et al, FEMS Microbiol. Lett., 15, 295–298 (1982).

Primary Examiner—Lionel M. Shapiro

[57] ABSTRACT

Enzymatic conversion of polysaccharides to monosaccharides or lower molecular weight polysaccharides is carried out by means of an enzyme derived from *B. megaterium* which exhibits alpha-amylase activity.

13 Claims, No Drawings

PROCESS OF ENZYMATIC CONVERSION OF POLYSACCHARIDES

FIELD OF THE INVENTION

The present invention relates to a process of enzymatic conversion, in particular, to the enzymatic conversion of polysaccharides such as starch or a partially hydrolyzed starch by means of an enzyme exhibiting alpha-amylase activity.

BACKGROUND OF THE INVENTION

Amylases are an important group of carbohydrases and have an extensive industrial use. They are characterized by the ability to hydrolyze the alpha-D-glucosidic linkage in starch compounds and commercially their principal outlet is in starch processing technology. Starch, which is a polysaccharide of considerable molecular weight may be hydrolyzed by means of an alpha-amylase to produce polysaccharides of lower molecular weight containing up to ten monosaccharide units. Such an enzyme is termed a "liquefying" enzyme since, by cleaving the starch molecule, it converts to liquid form a starch suspension or a thick starch paste. Other amylases catalyze different hydrolytic operations, for example, beta-amylase catalyzes hydrolysis at the nonreducing ends of starch, glycogen or dextrin molecules splitting off a maltose molecule while glucoamylase catalyzes the removal of glucose from the nonreducing ends of the same poly- or oligo-saccharides.

Enzymes exhibiting alpha-amylase activity are obtained from a variety of natural sources, e.g., from molds, fungi and bacteria and enzymes from different organisms although having alpha-amylase activity and being able to catalyze the hydrolytic reactions catalyzed in general by alpha-amylases frequently differ in the conditions under which they operate, particularly, conditions of temperature and pH and in industrial practice, such differences may be important.

In U.S. Pat. No. 4,469,791 is described inter alia, a process for producing enzymes with amylase activity from genetically-engineered microorganisms. A number of microorganisms are described in that patent which donate to the genetically-engineered microorganisms genes coding for a variety of enzymes which show amylase activity. One such donor microorganism disclosed in U.S. Pat. No. 4,469,791 is *B. megaterium* (*Bacillus megaterium*) although the enzyme produced from this microorganism is not described as having any properties which would single it out from other enzymes with amylase activity described as being capable of being produced by the process of the patent. We have now found, however, that the enzyme from *B. megaterium* which has alpha-amylase activity, possesses properties which make it of particular use in certain industrial applications.

SUMMARY OF THE INVENTION

Accordingly, the invention comprises a process for the enzymatic conversion of a polysaccharide to a monosaccharide or to one or more polysaccharides of lower molecular weight wherein the polysaccharide is contacted at a pH in the range 4.5 to 8.0 with an enzyme which derives from *B. megaterium* and which exhibits alpha-amylase activity.

DETAILED DESCRIPTION OF THE INVENTION

The *B. megaterium* is preferably that strain deposited in the National Collection of Industrial Bacteria, Aberdeen, Scotland, under the designation NCIB No. 11568.

The enzyme used in the process of the invention is capable of catalyzing the conversion of polysaccharides of different composition. Thus, although its prime commercial use is in the conversion of starch or partial starch hydrolyzates to a monosaccharide or to polysaccharides of lower molecular weight, it will also catalyze the conversion of pullulan, the product being almost entirely the trisaccharide, panose. Unlike other enzymes with alpha-amylase activity, the *B. megaterium* enzyme will also catalyze the hydrolysis of cyclodextrins to a product which ultimately consists largely of dextrose, maltose and maltotriose.

A particularly significant use of the *B. megaterium* enzyme is in a process to produce dextrose syrups from starch or starch hydrolyzates in which the hydrolysis reaction is catalyzed by a glucoamylase. The reaction conditions are chosen such that the *B. megaterium* enzyme and glucoamylase may be used together at the same time in the same medium. In particular, the *B. megaterium* alpha-amylase active enzyme may be added to a conventional saccharification reaction in which the feedstock is an aqueous dispersion of a maltodextrin or a liquefied starch and the hydrolytic enzyme a glucoamylase with the following unexpected advantages:

(a) For a given amount of glucoamylase, the saccharification time may be reduced or for a given saccharification time, the amount of glucoamylase used may be reduced.

(b) A higher concentration of dissolved solids in the feedstock may be used (up to 10 wt % more) to get a product with the same dextrose concentration. Alternatively or concomitantly, there may be produced from a feedstock with a standard concentration of dissolved solids or a feedstock with slightly increased dissolved solids, a product with an increased dextrose concentration (increased by 0.5 to 1 wt %) and a lower concentration of oligomers ($DP_n$ reduced to 0.2 wt %., where DP represents "dextrose polymer" and "n" the number of dextrose units in the polymer).

(c) The "alcohol turbidity", as hereinafter described, is reduced. "Alcohol turbidity" is indicative of the content in the saccharification product of oligomeric components.

The process in which glucoamylase and the *B. megaterium* enzyme are used together is preferably carried out at a temperature in the range 40° to 65° C., more preferably 55° to 60° C. The pH is preferably 4.5 to 5.5, more preferably about 5.0. In general, the lower the pH, the lower the temperature used and vice versa. The maltodextrin or liquefied starch feedstock may contain 20 to 40% by weight dissolved solids, particularly 25 to 35% by weight dissolved solids. The amount of glucoamylase which is employed is suitably 0.05 to 0.40%, preferably 0.10 to 0.20% by weight based on feedstock dry substance and the *B. megaterium* enzyme preferably 0.02 to 10.0, more preferably 0.1 to 2.0 units/gram of feedstock dry substance. The product obtained may contain more than 96 wt % dextrose, preferably more than 97 wt %, particularly more than 97.5 wt % dextrose.

The expression of the *B. megaterium* amylase active enzyme concentration in units/gram dry substance is conventional practice in enzyme technology and is necessary because enzyme samples may exhibit different activities depending, for example, on their purity, etc. The activity of a given sample is determined by the PHADEBAS test which employs a commercially-available test kit and which is based on the optical estimation of the strength of a dye liberated by the enzyme under carefully controlled conditions. If the activity of the enzyme is completely unknown, samples are first diluted with water to produce a range of dilutions which are then tested by the method described below to find the dilution which, under the test conditions, gives an optical density of the dye in the range suitable for quantitative determination. The test is then repeated at this concentration in comparison with a blank sample.

In detail, 200 microliters of diluted enzyme sample is placed in a test tube and mixed with 4 ml of buffer solution. The blank consists of 200 microliters demineralized water and 4 ml buffer solution. The buffer solution comprises sodium acetate (20 mM) and calcium chloride (2 mM) adjusted to pH 5. A PHADEBAS tablet, Pharmacia Diagnostics, Piscataway, N.J., is then added to each sample, the sample agitated for 10 seconds, and the sample placed in a well-stirred water bath where it is held at 55° C. for 15 minutes. The PHADEBAS tablet contains a dye and a buffer, the effect of the two buffer systems being to establish a final pH of 6.3 in the test solution.

After the 15-minute period, the reaction is stopped by adding 1 ml of 0.5 molar sodium hydroxide and the sample agitated before being centrifuged at approximately 1500 g for 5 minutes or filtered. The absorbance of the sample is then measured at 620 nm against demineralized water using a cuvette of 1-cm light path. The absorbance of the blank is subtracted from the sample under test and the amylase units of activity determined in units/liter from the PHADEBAS standard curve.

In addition to the use of the *B. megaterium* enzyme in the production of high dextrose syrups, the enzyme may also be used to improve the quality of dextrose syrups obtained by other processes. In particular, the "alcohol turbidity" of such syrups may be reduced by contact with the enzyme under pH and temperature conditions given above for the process using the glucoamylase *B. megaterium* enzyme combination. The "alcohol turbidity" may be reduced to a level such that, by subsequent treatment with ion exchangers, it may be eliminated altogether.

The invention will now be further described with reference to the following examples.

The apparatus used in the examples comprised a series of 500-ml Erlenmeyer flasks mounted on a shaking frame in a thermostatically-controlled water bath. In general, the feedstock comprised 500 ml of a maltodextrin solution containing 0.02 molar sodium acetate as a buffer to help maintain a stable pH. The solution also contained 80 mg $Ca^{++}$ liter (in the form of calcium chloride). An initial pH adjustment was made with acetic acid and the enzyme(s) added to initiate reaction. The reaction pH was controlled by measuring the pH of the solution with a meter twice daily and adding sodium hydroxide if the pH had fallen. A 100-ml sample was also withdrawn every 24 hours, the enzyme(s) denatured by boiling for 30 minutes and the denatured solution filtered. The dextrose content of the filtered sample was then determined by high-pressure liquid chromatography and where appropriate, an alcohol turbidity test was carried out.

"Alcohol turbidity" is measured by:
(a) placing a sample into a 100-ml flask so that there is present 0.91 g dissolved solids (as determined by refractometer),
(b) adding demineralized water so that the total water present is 3.39 g,
(c) adding 27 ml ethanol of 99.8% purity,
(d) boiling with stirring under reflux for 9 to 10 minutes,
(e) cooling under running water, and
(f) measuring the optical density at 578 nm in a 4-cm cell.

The glucoamylase used in the examples was OPTIDEX L150, supplied by Miles-Kali Chemie. (OPTIDEX is a trademark.)

EXAMPLE 1

Effect of the alpha-Amylase Active Enzyme from *B. megaterium* NCIB No. 11568 on the Glucoamylase-Catalyzed Hydrolysis of 18 D.E. (Dextrose Equivalent) Maltodextrin to Dextrose The feed solution contained 25% by weight dissolved solids and the temperature was maintained at 55° C. The hydrolysis with glucoamylase alone was carried out at the conventional pH for this reaction of 4.2. When the *B. megaterium* enzyme was added, the pH was increased to 5.0. The following Table I gives the dextrose contents of the product obtained after 48 hours.

TABLE I

| Glucoamylase Weight, % | *B. megaterium* Enzyme units/g of Maltodextrin | Dextrose Content Weight, % |
|---|---|---|
| 0.10 | — | 95.0 |
| 0.14 | — | 95.9 |
| 0.10 | 1.5 | 96.6 |
| 0.13 | 1.5 | 96.8 |

EXAMPLE 2

Effect of the alpha-Amylase Active Enzyme from *B. megaterium* NCIB No. 11568 on the Glucoamylase-Catalyzed Hydrolysis to Dextrose of 18 D.E. Maltodextrin at Increasing Dissolved Solids in the Reaction Solution The hydrolysis was carried out at 60° C. and pH 5. The amount of glucoamylase added was 0.075 wt % and the *B. megaterium* enzyme 1.5 units/g. The results are given in Table II.

TABLE II

| Maltodextrin % w/w Dissolved Solids | Time hrs | Dextrose Content Weight, % |
|---|---|---|
| 15 | 48 | 95.6 |
| 15 | 96 | 97.9 |
| 25 | 48 | 94.0 |
| 25 | 96 | 97.0 |
| 35 | 48 | 91.6 |
| 35 | 96 | 95.7 |

EXAMPLE 3

Effect of the alpha-Amylase Active Enzyme from *B. megaterium* NCIB No. 11568 on the Glucoamylase-Catalyzed Hydrolysis of 18 D.E. Maltodextrin to Dextrose at 60° C. and Varying Glucoamylase Concentrations The solution contained 25% by weight dissolved solids, the pH was 5 and the concentration of the *B. megaterium* enzyme was 1.5 units/g. The results after 72 hours were as follows in Table III.

TABLE III

| Glucoamylase Weight, % | Dextrose Content Weight, % |
|---|---|
| 0.10 | 97.2 |
| 0.08 | 96.9 |
| 0.05 | 93.1 |

EXAMPLE 4

Effect of the alpha-Amylase Active Enzyme from *B. megaterium* NCIB No. 11568 on the Glucoamylase-Catalyzed Hydrolysis of 12 D.E. Maltodextrin at 55° C. and Varying pH The buffer in this series of experiments was 0.1 molar sodium acetate, the concentration of the glucoamylase 0.15 wt %, and the *B. megaterium* enzyme 1.5 units/g. The results after 48 hours are given below in Table IV.

TABLE IV

| pH | Dextrose Content Weight, % |
|---|---|
| 4.6 | 96.0 |
| 4.8 | 96.6 |
| 5.0 | 96.8 |
| 5.2 | 96.4 |
| 5.4 | 96.1 |

EXAMPLE 5

Effect of the alpha-Amylas Active Enzyme from *B. megaterium* NCIB No. 11568 on the Glucoamylase-Catalyzed Hydrolysis of 18 D.E. Maltodextrin at 55° C. and pH 5 with Varying Amounts of Glucoamylase and *B. megaterium* Enzyme The results are given below in Table V.

TABLE V

| Glucoamylase Weight, % | *B. megaterium* Enzyme units/g of Maltodextrin | Time hrs | Dextrose Content Weight, % |
|---|---|---|---|
| 0.10 | 0.75 | 72 | 97.1 |
| 0.10 | 1.5 | 72 | 97.0 |
| 0.075 | 0.75 | 96 | 97.5 |
| 0.075 | 1.5 | 96 | 97.3 |
| 0.05 | 1.5 | 96 | 97.3 |
| 0.05 | 3.0 | 96 | 96.7 |
| 0.04 | 6.0 | 96 | 95.8 |
| 0.03 | 6.0 | 96 | 93.1 |

EXAMPLE 6

Effect of the alpha-Amylase Active Enzyme from *B. megaterium* NCIB No. 11568 on the Hydrolysis of alpha-Cyclodextrin The reaction solution contained 15% dissolved solids and it was maintained at 60° C. and pH 6 in the presence of varying amounts of the *B. megaterium* enzyme. The results after 240 hours are given below in Table VI.

TABLE VI

| Concentration of *B. megaterium* Enzyme units/g Cyclodextrin | Dextrose Content Weight, % |
|---|---|
| 15 | 44.8 |
| 30 | 77.7 |

EXAMPLE 7

Comparative Experiment Using a Commercially-Available alpha-Amylase in Combination with Glucoamylase The reaction conditions were the same as Example 1 except that the feed solution contained 32% by weight dissolved solids. The results after 96 hours are given in Table VII and show that unlike the alpha-amylase active enzyme derived from *B. megaterium*, the commercial alpha-amylase confers no improvement on the glucoamylase hydrolysis, even after 96 hours. (The commercial alpha-amylase used in this and the next example was TERMAMYL 60L, available from Novo Laboratories, Inc., Wilton, Conn.)

TABLE VII

| | Glucoamylase 0.18 wt % | Glucoamylase 0.18 wt % plus | |
|---|---|---|---|
| | | A | B |
| Dextrose in Product (Weight, %) | 93.7 | 93.6 | 94.3 |
| Alcohol Turbidity | 0.240 | 0.490 | 0.043 |

A = 5.6 units of a commercially-available alpha-amylase per gram of maltodextrin
B = 1.5 units of the alpha-amylase active enzyme of *B. megaterium* NCIB No. 11568 per gram of maltodextrin

EXAMPLE 8

A sample of dextrose syrup which had been produced by a glucoamylase-catalyzed hydrolysis contained 95.8% by weight dextrose and had an alcohol turbidity of 1.550.

The sample was divided into two parts. One part was subjected to treatment at 55° C. and pH 5.0 with the alpha-amylase active enzyme of *B. megaterium* NCIB No. 11568. The other part was subjected to the same treatment with a commercially-available alpha-amylase. The results of the treatment are given in Table VIII.

TABLE VIII

| | alpha-Amylase Active Enzyme from *B. megaterium* | | Commercially-Available alpha-Amylase | | |
|---|---|---|---|---|---|
| | 0.25 U/g | 0.5 U/g | 0.075 U/g | 0.15 U/g | 0.3 U/g |
| Dextrose | 95.5 | 95.3 | 95.7 | 95.5 | 95.3 |
| Alcohol Turbidity | 0.176 | 0.045 | 1.410 | 1.380 | 1.240 |

U/g = units/gram of syrup on a dry solids basis

EXAMPLE 9

A solution of pullulan containing 5% by weight dissolved solids was treated at 55° C. and pH 5.6 for 24 hours with 50 units/g of dry substance of the alpha-amylase active enzyme from *B. megaterium* NCIB 11568. At the end of the 24 hours, the pullulan was converted to 98% by weight pannose.

Thus, there has been provided, in accordance with this invention, a process for the enzymatic conversion of polysaccharides. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. An enzymatic process for the production of dextrose syrup from a starch hydrolyzate wherein the starch hydrolyzate is contacted at a pH in the range 4.5 to 8.0 with glucoamylase together with an enzyme derived from *Bacillus megaterium* and which exhibits alpha-amylase activity.

2. A process according to claim 1 wherein the *Bacillus megaterium* is *Bacillus megaterim* NCIB No. 11568.

3. A process according to claim 1 wherein the starch hydrolyzate is an aqueous dispersion of maltodextrin or a liquefied starch.

4. A process according to claim 3 wherein the temperature is in the range 40° to 65° C., preferably 55° to 60° C.

5. A process according to claim 3 wherein the pH is 4.5 to 5.5, preferably about 5.0.

6. A process according to claim 3 wherein the amount of glucoamylase which is used is 0.05 to 0.40, preferably 0.10 to 0.20% by weight of said maltodextrin or liquefied starch on a dry solids basis.

7. A process according to claim 3 wherein the amount of enzyme derived from *Bacillus megaterium* which is used is 0.02 to 10.0, preferably 0.1 to 2.0 units per gram of maltodextrin or liquefied starch on a dry solids basis.

8. A process according to claim 3 wherein the aqueous dispersion of maltodextrin or liquefied starch contains 20 to 40% by weight, preferably 25 to 35% by weight, of said maltodextrin or liquefied starch on a dry solids basis.

9. A process according to claim 8 wherein the temperature is in the range 40° to 65° C., preferably 55° to 60° C.

10. A process according to claim 8 wherein the pH is 4.5 to 5.5, preferably about 5.0.

11. A process according to claim 8 wherein the amount of glucoamylase which is used is 0.05 to 0.40, preferably 0.10 to 0.20% by weight of said maltodextrin or starch on a dry solids basis.

12. A process according to claim 8 wherein the amount of enzyme derived from *Bacillus megaterium* which is used is 0.02 to 10.0, preferably 0.1 to 2.0 units per gram of maltodextrin or liquefied starch on a dry solids basis.

13. A process wherein an enzyme derived from *Bacillus megaterium* which exhibits alpha-amylase activity is contacted with a dextrose syrup which exhibits alcohol turbidity so that the alcohol turbidity is reduced.

* * * * *